United States Patent [19]

Tronzo

[11] Patent Number: 4,653,489
[45] Date of Patent: Mar. 31, 1987

[54] FENESTRATED HIP SCREW AND METHOD OF AUGMENTED FIXATION

[76] Inventor: Raymond G. Tronzo, 255 Clarke Ave., Palm Beach, Fla. 33480

[21] Appl. No.: 859,225

[22] Filed: May 5, 1986

Related U.S. Application Data

[63] Continuation of Ser. No. 595,240, Apr. 2, 1984, abandoned.

[51] Int. Cl.⁴ .............................................. A61F 5/04
[52] U.S. Cl. ............................ 128/92 YV; 128/92 VQ
[58] Field of Search .......... 128/92 VP, 92 VO, 92 V, 128/92 YV

[56] References Cited

U.S. PATENT DOCUMENTS 4,494,535 1/1985 Haig ................................ 128/92 BA

OTHER PUBLICATIONS

Zimmer USA, Warsaw, Ind., 46580, 1981 Catalog p. A208, "L.V.C. Bone Cement".
Brochure from KNY-Scheerer Corp. "New Instruments for the Operative Treatment of Fractures of the Neck of the Femur", Moreira, 1941.
Mueller & Co., Catalog, "Bone Surgery Instruments", p. 7, 1937.

Primary Examiner—C. Fred Rosenbaum
Assistant Examiner—C. W. Shedd
Attorney, Agent, or Firm—Eugene Chovanes

[57] ABSTRACT

A fenestrated hollow hip screw adapted for introduction therethrough of bone cement into a bone region affected by osteoporosis for increase of overall fixation of hip fractures, such as comminuted intertrochanteric types, and similar types of femoral fractures, even in the opposite distal end of the femur where such a device may be appropriately utilized.

4 Claims, 4 Drawing Figures

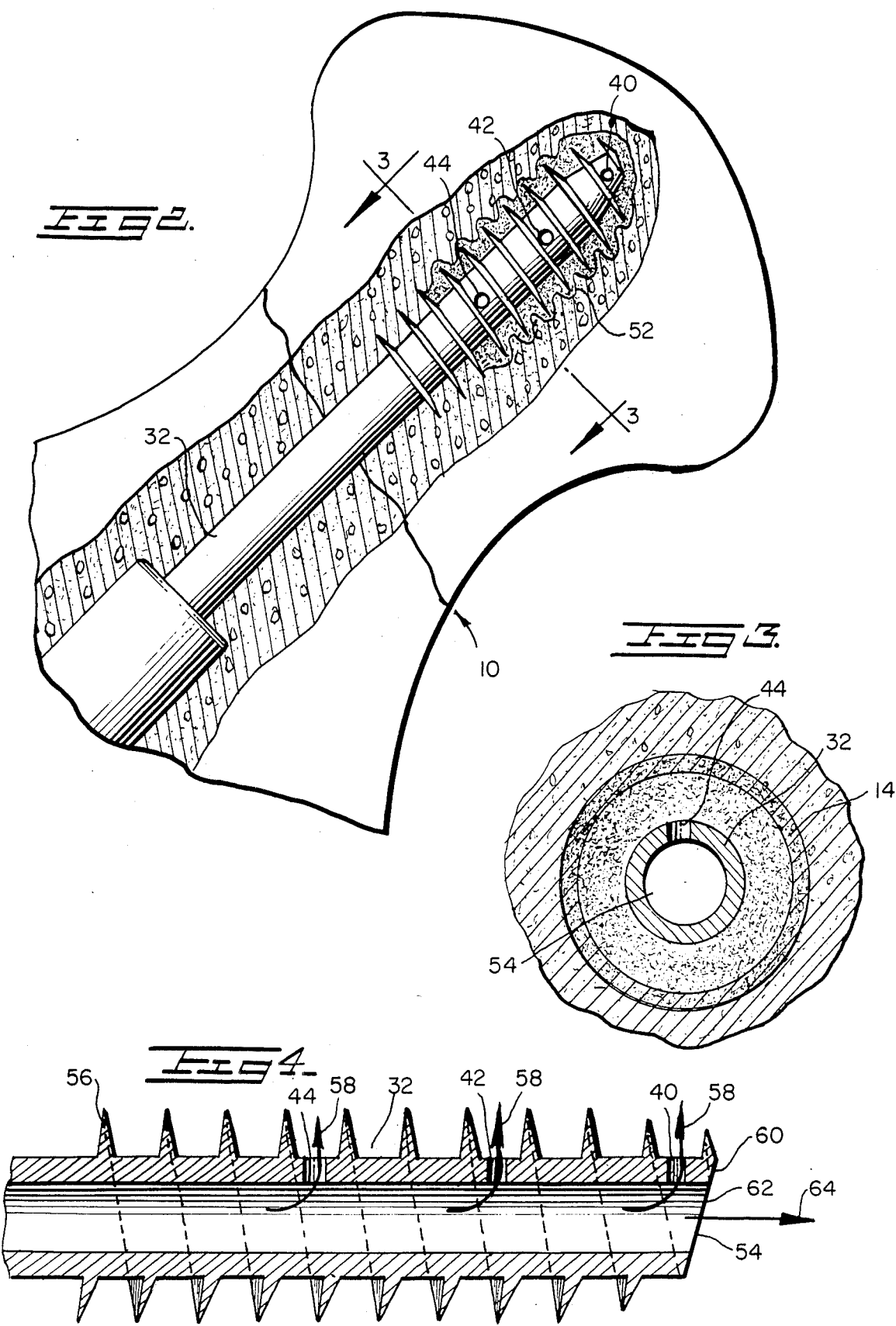

ic fractures of the upper end of the femur. Despite nail fixations and biomechanics appropriately applied, such fractures have continued to cause problems due to the screw being able to cut out of the head with a loss of reduction and consequent disastrous results. The present invention teaches an option for solving this problem, i.e., a fenestrated hip screw for use
FENESTRATED HIP SCREW AND METHOD OF AUGMENTED FIXATION This application is a continuation of application Ser. No. 595,240, filed Apr. 2, 1984, now abandoned.

FIELD OF THE INVENTION

The present invention relates to augmenting internal fixation of hip fractures, especially intertrochanteric types by utilization of a fenestrated hip screw through which a fixing cement can be introduced into a region of the bone where a problem of osteoporosis exists. Femoral neck fractures as well as distal femoral fractures may be likewise fixed with this device.

Severly comminuted intertrochanteric fractures pose a serious challenge to medical practitioners in the field of orthopedics despite advances which have been made in the biomechanical design of fixation devices. A popular and widely used internal device for repair of such fractures is a sliding lag screw. It has been found, however, that in spite of use of such biomechanical advances and in spite of a better understanding of these fractures, problems remain when conditions of osteoporosis are severe and which tend to defeat overall successful fixation of fractures of this type.

The invention is particularly of significance in the repair of upper femoral fractures when dealing with complicated patterns and high degrees of osteoporosis in the bone structure. Techniques exist for appraising the degree of osteoporosis such as the Singh Index. The information obtained is correlated closely with the comminution and consequent instability of intertrochanteric fractures. Different degrees of osteoporosis must be determined and repair of a fracture correlated with this information.

Under conditions where osteoporosis is not severe or diffuse, comminution can be practically reduced through use of nailing using pins and screws. Under some conditions where severe osteoporosis exists, however, instances of loss of reduction can occur and refractures under such conditions are difficult if not impossible of restoration without resorting to the use of some type of hip arthroplasty.

Heretofore, internal fixation in severly osteoporotic, comminuted, unstable intertrochanteric fractures has been augmented by packing cements such as methylmethacrylate around the implant in a rather crude manner. Problems exist, however, with putting or placing such cements into the fracture sight by occurrence of nonunion. It has been found that extreme care must be taken to insure that the cement does not get extruded between the main fracture fragments, since otherwise, the foreign body will absolutely prohibit boney union. It has likewise been found that such procedures can entail the cumbersome addition of windowing the interior fracture sight and packing the cement into a less than ideal position, with the windowing creating a weakness to the overall strength of the bone.

Under some circumstances the use of methacrylate as an adjunct in comminuted trochanteric fractures especially in patients of older ages has been proposed. The proposals included the use, for example, of a combination of a blade plate and packing methacrylate into the upper end of the femur to achieve a plurality of desired end results. These included a stable fixation of metal implants; the reconstruction of the important posteromedial cortical wall; and the ability to bear weight immediately. In practicing this technique, a cavity was cut out in the head, neck, and trochanter into which the acrylic was packed, followed by the insertion of a blade plate. In use, such techniques were found to provide highly improved fixation with substantially no complications during the lifespan of patients.

While techniques utilizing cements have been in use and a measure of success noted, there have been difficulties encountered and it is the intent of the present invention to provide a highly successful cement technique utilizing a certain type of screw instead of any blades or so-called tri-flanged nails. While the present invention will be specifically described in a single preferred constructional form, obviously the invention is not limited to the specific structure and variations in specifics of constructional details and materials will be obvious and within the scope of the invention as defined by the claims herein.

BRIEF DESCRIPTION OF THE DRAWINGS

The accompanying drawings illustrate the preferred embodiment of the invention, and when taken together with the following description, serve to explain the principles and concept of the invention. In the drawings:

FIG. 2 is a fragmentary enlarged view of a portion of a lag screw utilized in practicing the invention, this figure emphasizing details of the use of the head of the screw in practicing the technique of cement introduction for enhanced fixation of the pin utilized in reduction of the fracture;

FIG. 3 is a sectional enlarged view taken on line 3—3 of FIG. 2; and

FIG. 4 is an enlarged sectional view through the end of a lag screw including fenestrations for practicing the present invention.

SUMMARY OF THE INVENTION

Figure 1:
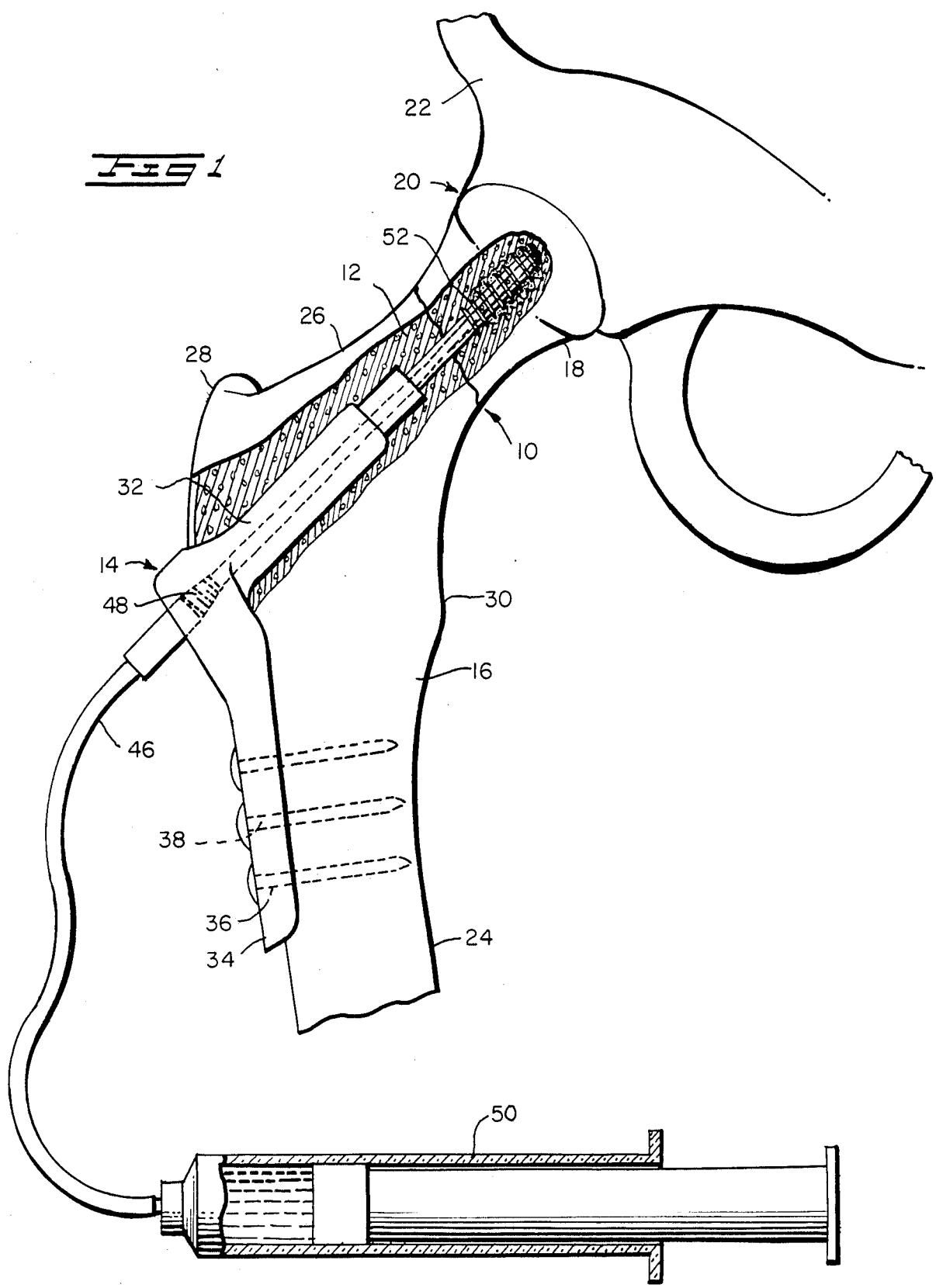
FIG. 1 is a schematic view illustrating the concept and structure of the invention, parts being broken away and in section to facilitate an understanding of the invention.

The present invention has simplicity and utilization of known mechanisms and techniques to provide improved results in repair or reduction of bone fractures as discussed above but useful in other instances.

Basically the invention teaches use of a sliding or collapsible hip screw device of a known type but which has been fenestrated in a region desirable for the injection of cement whenever indicated. The essential keystone of this invention is the fenestration between the screw blades so that cement can be injected into the femoral head and away from the fracture site as such, further locking the screw threads into the bone. It is important to note that screw threads rather than any nail blades cut out spiral grooves along which a better penetration and a more evenly controlled injection of cement can occur for more reliable implant - cement/bone fixation.

It is known that osteoporosis is a very definite factor in the causation of severe comminution and instability in intertrochanteric fractures of the upper end of the femur. Despite nail fixations and biomechanics appropriately applied, such fractures have continued to cause problems due to the screw being able to cut out of the head with a loss of reduction and consequent disastrous results. The present invention teaches an option for solving this problem, i.e., a fenestrated hip screw for use in augmenting fixation by way of injection methylmethacrylate into an appropriate area for enhanced fixation and a solution of existing problems.

DESCRIPTION OF THE PREFERRED EMBODIMENT

Referring now specifically to the drawings, there is disclosed in FIG. 1 a view similar to an X-ray of a hip fracture generally indicated at 10 either located in the femoral neck or in the intertrochanteric area.

A substantial or marked degree of osteoporosis in the region generally designated 12 may be present. The hip-pinning device generally designated 14 is depicted in connection with and in use in a femur or thigh bone 16. The upper extremity of the thigh bone or femur comprises a rounded head 18 which articulates within the cavity generally indicated at 20 within a hip bone 22. The rounded head 18 is joined to a shaft portion 24 by a constructed neck 26, the base portion of which lies adjacent to projections or emminences known as greater and lesser trochanters 28 and 30 respectively all as well known. Fractures of the femur usually occur in the restricted portion or neck 26, for example, as indicated at 10 and in a plane substantially transverse of the neck, or in a plane at a different angle to the axis of the neck.

Reference is here made to U.S. Pat. No. 3,554,193 issued Jan. 12, 1971 to Konstantinou et al., which refers to and depicts a similar type of fracture to that shown in the drawing and this patent shows utilization of a fixation pin and associated components for reduction of the fracture.

In accordance with the present invention, however, a sliding hip screw 32 is utilized and which device has longer threads which increase the nail stoutness, but more importantly, the cannulation is large. The basic or underlying technique is well known and in current use and basically is illustrated in the aforementioned patent. The lag screw as is well known includes an elongated plate 34 of a shape conforming to the outer face of the thigh bone 24 and includes a plurality of openings at 36 for insertion therethrough of screws 38 for fixation of the lag screw device in an usual and known manner.

Insertion and attachment of the lag screw is effected in the usual well known manner and as shown in the drawings, the fracture is well reduced by the pin located across the fracture and fixed within the surrounding bone portions. An osteoporosis condition exists, however, and it is therefore desirable that methylmethacrylate cement be utilized for enhanced fixation of the screw in the femoral head in such a way that the cement in the fins of the screw will prevent the screw from cutting itself out of the osteoporotic bone. It is known that the unique feature of lag screws is that the sharp blades of the screw can easily cut through the soft osteoporotic bone unless otherwise blocked by the cement injected through the fenestration. A known sliding screw is utilized in the present invention by placement or formation of a plurality of fenestrations indicated at 40, 42 and 44.

Use of the sliding hip screw of a known type very conveniently allows for routine use of a standard intravenous (IV) extension tube 46 which is oepratively associated at 48 with the cannula or bore of the screw. In operation this extension tube permits the injection of the methylmethacrylate in its liquid form. The extension tubing conveniently screws into the threads of the barrel as indicated at 48. In practice a half of a pack of powdered methylmethacrylate is poured into a 20 cc syringe 50 and a half of liquid monomer portion of the methylmethacrylate is poured into the syringe. The powder and the liquid are mixed and, while still very liquid, it is forced into the cannulated barrel of the screw and then out through the fenestrations of the lag screw.

Methylmethacrylate becomes extruded mostly at the mid-fenestration rather than at the tip. This is significant since, in practice, the methylmethacrylate is needed in a pattern as shown generally at 52 in FIG. 2. The cement accordingly passes through the cannula or bore 54 of the screw device 32 which, as is also usual, includes plural threads 56 of a type permitting threading into the interior bone structure by utilization of a guide wire in a known manner and which therefore fix the pin in place with appropriate reduction of the fracture. As is well known, the type of thread is such as to permit a reverse cutting movement through the cement for removal of the screw if later required for further treatment of the fracture.

The flow path of the methyl methacrylate cement is indicated by arrows designated 58 transversely through the fenestrations 40, 42 and 44. It is also seen that the end 60 of the lag screw provides an open end 62 for the bore or cannula 54 and arrow 64 indicates a flow of methylmethacrylate cement therefrom. With this type of flow the pattern of injected cement assumes the configuration designated 52.

As noted above, this very pattern is desirable because if the hip screw is placed just subchondral in this part of the bone, it might provide little extrusion of the cement into the hard bone. The fenestrations do not go into the most distal threads so that the methylmethacrylate will not flow around the threads only, which would jeopardize the sliding mechanism. And further, the cement thus injected does not flow between the fracture fragments.

It has been found that in some instances, despite excellent reduction and excellent position of the fragments, softness of the bone could be felt. With much compression, the screw can pull out of the soft head. At this point, methylmethacrylate is injected, for example into the fenestrated screw and a predetermined amount of bone cement injected into the femoral head. The fracture under such circumstances normally will heal with no loss of fixation.

A definitely sequenced practiced cementing technique must be utilized and a strict sequence of steps must be followed when injecting the fenestrated nail according to the invention. It is theoretically possible to have the cement inject itself into the head and pour out into the joint space. A second potential problem is that the cement may flow backward around the barrel, thus preventing the fracture from collapsing on itself.

For these reasons, the following sequence must be followed:

(1) The fracture is gently compressed with the compression device as far as possible without taking a real hard turn.

(2) The leg is moved slightly so the guide pin hole has been displaced away from its mate across the joint.

(3) The methylmethacrylate is injected into the femoral head via the nail. This will prevent any cement from flowing around the barrel of the screw, which would prevent subsequent sliding. In some instances it has been found remarkable how much liquid cement will be accepted by some osteoporotic femoral heads, usually anywhere from 3–6 cc.

(4) The wound is then closed in layers.

There are two situations that provide the surgeon with the option to use methylmethacrylate to augment the fixation of the fenestrated screw. The first is that he can predict from the Singh index the degree of osteoporosis. Thus, he can anticipate using the augmentation of cement routinely if the Singh index is, as understood in the practice, either Grade 1, 2 or 3. The second is when the placement of the nail is less than ideal and the surgeon does not wish to reinsert the screw in order to prevent further destruction of the head fragment.

In practice, the utilization of the foregoing described technique resulting from the fenestrations in the lag screw to augment fixation of a fenestrated screw have been highly successful. Under conditions of osteoporotic soft heads, the option of using methylmethacrylate has been excellent and provides high prophylaxis for preventing the nail from cutting out of the femoral head.

As a point of interest the retrievability of the screw which has been augmented with methylmethacrylate has been considered. This would seem to be a realistic problem should the screw have to be removed. The usual device, however, incorporates back threads which are cutting threads and removal could be effected if necessary for further and/or other treatment of the fracture.

In use, there has been no indication of weakness from the fenestrations of the threaded portion of the nail. As a matter of fact, where cement is injected around the threads, the cement itself adds strength to the metal cement complex.

Convenience to the surgeon also resides in the fact that occasionally the placement of the guide pin is not always as ideal as one would like it to be but which is only perceived after the nail is screwed into the head. Under such circumstances, if a fenestrated screw has been used or if available and cement injected into the femoral head, the fracture would be properly reduced and no failure would occur.

Accordingly the present invention provides an option for solving osteoporosis problems by utilization of a fenestrated hip screw for the use of augmenting the fixation by way of injecting methylmethacrylate as above related.

While a specific embodiment of the invention is disclosed in the drawings and described hereinabove, minor variations will be obvious to those skilled in the art without departing from the spirit of the invention. Such obvious changes or modifications are considered to be within the scope of the inventive concept as expressed herein, and as claimed hereinafter.

What is claimed is:

1. A hip screw for reducing bone fractures under highly advanced conditions of bone osteoporosis, comprising
   (a) an elongated body including a forward portion and a rear portion, said body containing a continuous through-bore extending between said forward and rear portions, said forward portion containing at the remote end thereof an opening communicating with said through-bore;
   (b) said body forward portion including an external spiral screw thread having a plurality of longitudinally spaced turns extending generally transversely of said elongated body;
   (c) said body portion containing a plurality of longitudinally spaced fenestrations in one side thereof and communicating with said through-bore, each of said fenestrations being arranged between a pair of adjacent turns of said screw thread; and
   (d) means connected with said body rear portion for delivering bone cement material to said through-bore, said cement material passing through said through-bore and exiting said body via said fenestrations and said forward portion open end, said spiral screw thread assisting the distribution of said cement material in a pattern surrounding said body forward portion to prevent said screw thread from being removed from the osteoporotic bone during healing of the fracture.

2. Apparatus as defined in claim 1, wherein said cement material comprises mixed components operable to form methylmethacrylate in a liquid form prior to setting and hardening.

3. Apparatus as defined in claim 1, wherein said cement material delivery means comprises a tube having one end threadably connected with said body rear portion and a syringe connected with the other end of said tube, said methylmethacrylate being arranged in said syringe in liquid form.

4. In a hip screw for reducing bone fractures under highly advanced conditions of bone osteoporosis including an elongated body having forward and rear portions and an external spiral screw thread arranged on the body forward portion and having a plurality of longitudinally spaced turns,
   the improvement wherein
   (a) the elongated body contains a continuous through-bore extending between the forward and rear portions;
   (b) the body forward portion contains at the remote end thereof an opening communicating with said through-bore;
   (c) the body forward portion contains a plurality of longitudinally spaced fenestrations in one side thereof and communicating with said through-bore, each of said fenestrations being arranged between a pair of adjacent turns of the screw thread; and
   (d) means are connected with the body rear portion for delivering bone cement material to said through-bore, said cement material passing through said through-bore and exiting said body via said fenestrations and said forward portion open end, the spiral screw thread assiting the distribution of said cement material in a pattern surrounding the body forward portion to prevent the screw thread from being removed from the osteoporotic bone during healing of the fracture.

* * * * *